(12) United States Patent
Pfeil et al.

(10) Patent No.: US 10,981,844 B2
(45) Date of Patent: Apr. 20, 2021

(54) SEMI-CONTINUOUS CRYSTALLIZATION METHOD AND APPARATUS

(71) Applicant: Sulzer Chemtech AG, Winterthur (CH)

(72) Inventors: Mathias Pfeil, Winterthur (CH); Manfred Stepanski, Buchs (CH)

(73) Assignee: Sulzer Management AG, Winterthur (CH)

( * ) Notice: Subject to any disclaimer, the term of this patent is extended or adjusted under 35 U.S.C. 154(b) by 157 days.

(21) Appl. No.: 15/736,070

(22) PCT Filed: Jun. 16, 2016

(86) PCT No.: PCT/EP2016/063889
§ 371 (c)(1),
(2) Date: Dec. 13, 2017

(87) PCT Pub. No.: WO2016/207056
PCT Pub. Date: Dec. 29, 2016

(65) Prior Publication Data
US 2018/0179121 A1 Jun. 28, 2018

(30) Foreign Application Priority Data

Jun. 24, 2015 (EP) .................................... 15173637

(51) Int. Cl.
*C07B 63/00* (2006.01)
*B01D 9/00* (2006.01)
(Continued)

(52) U.S. Cl.
CPC .............. *C07B 63/00* (2013.01); *B01D 9/004* (2013.01); *B01D 9/0013* (2013.01); *C07C 7/14* (2013.01);
(Continued)

(58) Field of Classification Search
None
See application file for complete search history.

(56) References Cited

U.S. PATENT DOCUMENTS 3,219,722 A 11/1965 Jakob
7,102,029 B2 * 9/2006 Ohkoshi .............. B01D 9/0059
562/485
(Continued)

FOREIGN PATENT DOCUMENTS

CN 1050829 A 4/1991
CN 202191722 U 4/2012
(Continued)

*Primary Examiner* — Tam M Nguyen
(74) *Attorney, Agent, or Firm* — Larson & Anderson, LLC

(57) ABSTRACT

A process for the separation of a substance from a liquid feed mixture and for the purification of the substance by fractional layer crystallization, wherein the liquid feed mixture comprises the substance to be separated and purified in a concentration of less than 50% by weight, which comprises the subsequent steps in the given order: (a) feeding the liquid feed mixture into a crystallization zone, in which at least one surface is provided, so that at least a part of the surface contacts the liquid feed mixture, (b) cooling the at least one surface of the crystallization zone to a temperature below the equilibrium freezing temperature of the liquid feed mixture so that a crystal layer enriched in the substance to be separated and purified is deposited on the at least one cooled surface, whereby a mother liquid having a lower concentration of the substance to be separated and purified than the liquid feed mixture is formed from the liquid feed mixture, (c) removing at least a portion of the mother liquid from the crystallization zone, (d) adding a further portion of liquid feed mixture into the crystallization zone, (e) allowing further deposition of a crystal layer enriched in the substance to be separated and purified to take place on the at least one
(Continued)

Figure 1:
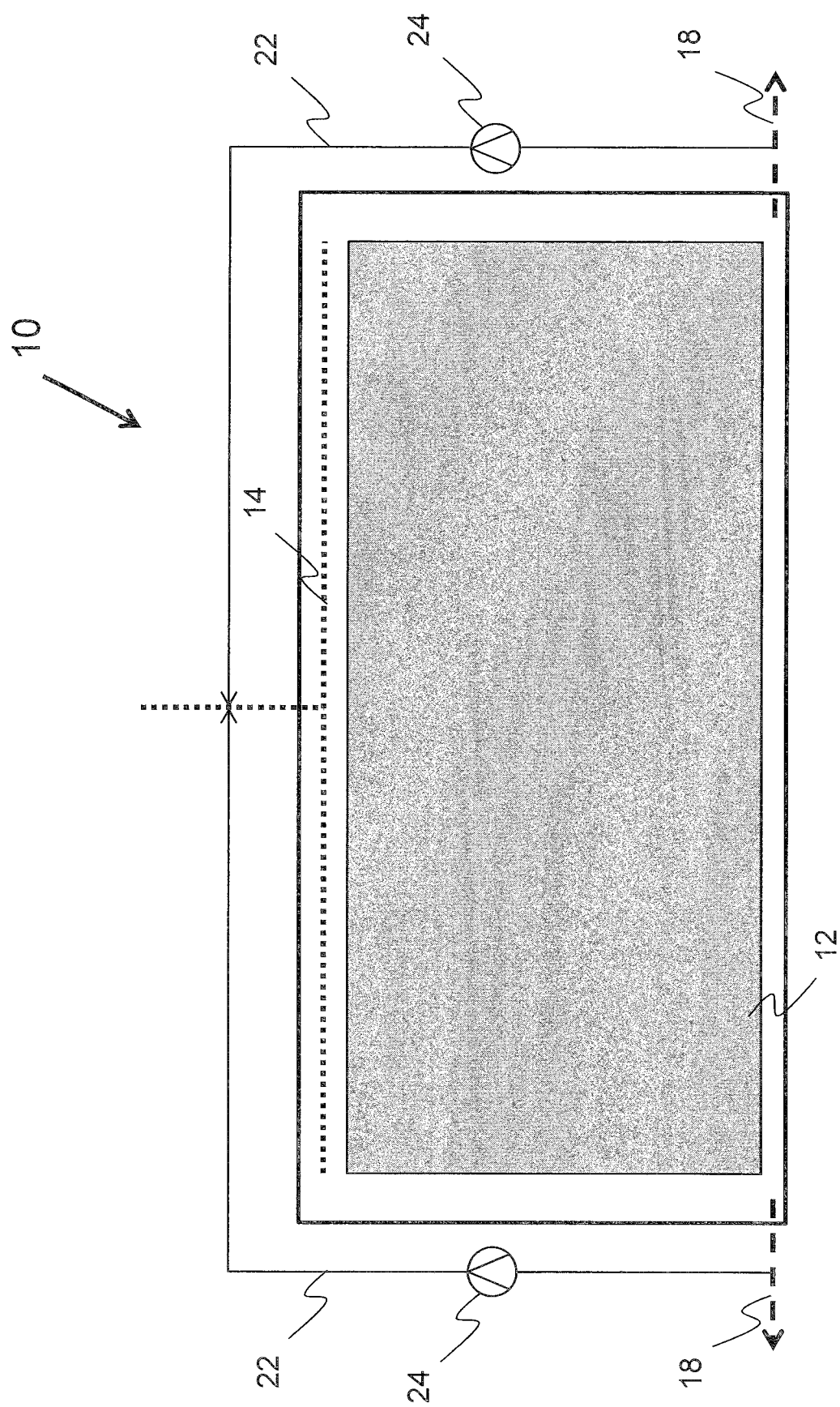

cooled surface, (f) optionally carrying out a sweating stage and removing a sweating residue and (g) melting the crystal layer to obtain the separated and purified substance.

2 Claims, 3 Drawing Sheets

(51) Int. Cl.
*C07C 7/14* (2006.01)
*C07C 51/43* (2006.01)

(52) U.S. Cl.
CPC ...... *C07C 51/43* (2013.01); *B01D 2009/0086* (2013.01)

(56) References Cited

U.S. PATENT DOCUMENTS

| | | | | |
|---|---|---|---|---|
| 2011/0061205 | A1* | 3/2011 | Scholz | B01D 9/0022 23/299 |
| 2013/0230446 | A1* | 9/2013 | Hofmann | B01D 9/0036 423/388 |
| 2015/0166721 | A1 | 6/2015 | Stepanski et al. | |

FOREIGN PATENT DOCUMENTS

| | | |
|---|---|---|
| CN | 103657137 A | 3/2014 |
| GB | 1229022 A | 4/1971 |
| WO | 01/21572 A1 | 3/2001 |

* cited by examiner

SEMI-CONTINUOUS CRYSTALLIZATION METHOD AND APPARATUS

The present invention relates to a process and an apparatus for the separation of a substance from a liquid feed mixture and for the purification of the substance by crystallization and particularly by fractional layer crystallization, wherein the liquid feed mixture comprises the substance to be separated and purified in a concentration of less than 50% by weight.

Crystallization is beside distillation and extraction one of the most important industrial processes for separating and purifying a substance from a mixture, in which the substance to be purified is contained in a high, medium or even low concentration. More specifically, solid crystals enriched in the substance to be separated and purified precipitate during crystallization from a solution or melt, provided that the substance to be separated and purified has in pure form a higher freezing temperature than the mixture of this substance with the other substances included in the solution or melt, respectively. Because crystallization has in comparison with particularly distillation the advantages of being able to be used for the separation and purification of heat-sensitive substances at comparable low temperatures, of needing merely comparable cost efficient equipment and of being comparable energy efficient, crystallization processes gain increasing importance in industry.

Usually, crystallization processes are subdivided in layer crystallization and in suspension crystallization.

During suspension crystallization a melt including at least two different compounds is cooled in a vessel so that crystals are formed resulting in a suspension of crystalline particles, which are enriched in the substance to be purified and which are dispersed in the melt depleted of the substance to be purified. Alternatively to cooling, the precipitation of the crystals may be effected by increasing the solute concentration above the solubility threshold by evaporating one of the compounds of the mixture. After completion of the crystallization, the crystals are separated from the suspension and, if necessary, further purified, such as in a second crystallization step or by means of another purification method.

In contrast to this, during a fractional layer crystallization crystals grow on a cooled wall surface, wherein the generated crystallization heat is conveyed through the crystal layers. Due to this, the crystals are cooler than the melt in a fractional layer crystallization method, whereas the crystals have at least substantially the same temperature than the melt in a suspension crystallization method. On account of this reason, a temperature gradient is generated between the crystal layer and the melt during a fractional layer crystallization method, wherein this temperature gradient is the driving force for the crystallization. Fractional layer crystallization processes are of particular industrial importance.

At present, two general kinds of fractional layer crystallization are known, namely static crystallization and falling film crystallization, which are typically both performed as batch processes.

For instance, a falling film crystallization process is typically performed in a crystallization vessel, which comprises tubes being arranged at least substantially vertically and extending from the upper part of the crystallization vessel into the bottom area of the crystallization vessel. Liquid feed mixture including the substance to be separated and purified in a certain concentration together with one or more other (undesired) substances is filled into the bottom area of the crystallization vessel, before the crystallization process is started. During the crystallization process, a portion of this liquid feed mixture is pumped by means of one or more pumps continuously from the bottom area of the crystallization vessel to the upper part of the crystallization vessel and is introduced into the upper end of the tubes and allowed to fall down the tubes as falling film back to the bottom area of the crystallization vessel. Concurrently, the outer walls of the tubes are cooled to a temperature below the equilibrium freezing temperature of the liquid feed mixture by allowing a cold heat transfer medium to flow as falling film down the outer surfaces of the tubes so that a crystal layer enriched in the substance to be separated and purified is deposited on the cooled inner wall surfaces of the tubes. As a consequence of the deposition of crystals of the substance to be separated and purified on the cooled inner wall surfaces of the tubes leading to a depletion of this substance in the liquid mixture, a mother liquid is formed from the liquid feed mixture, which has a lower concentration of the substance to be separated and purified than the liquid feed mixture. The circulation of the mother liquid is conducted as long as necessary to separate the desired amount of substance to be separated and purified from the mother liquid and to deposit it as crystals on the inner wall surfaces of the tubes. After completion of the crystallization, the mother liquid is completely removed from the crystallization vessel, the crystallization layers deposited on the inner wall surfaces of the tubes are melted and then removed from the crystallization vessel in order to obtain the separated and purified substance. Optionally, in order to increase the purity of the target product the crystallization layers may be sweetened by gently heating them to a temperature close to the melting temperature of the purified substance in order to partially melt the crystals, before melting them. If necessary, the obtained substance may be further purified by another crystallization process or by a different process, such as distillation. Due to the fact that liquid phase is continuously and forcibly moved through the tubes and thus around the crystal layers, falling film crystallization is considered as a dynamic crystallization process.

In contrast to falling film crystallization, the liquid phase is not moved during static crystallization and thus the crystals are formed and grown in a static liquid phase.

More specifically, a typical static crystallizer comprises a plurality of walls, such as plates, which can be cooled and heated by circulating a heat transfer medium through the interior of the plates. At the beginning, the static crystallizer is filled with liquid feed mixture including the substance to be separated and purified in a certain concentration together with one or more other (undesired) substances so that the plates contact the liquid feed mixture. Then, the plates of the static crystallization vessel are cooled to a temperature below the equilibrium freezing temperature of the liquid feed mixture so that crystals enriched in the substance to be separated and purified are formed and deposited on the cooled outer surfaces of the plates. Again, as a consequence of the deposition of the substance to be separated and purified on the cooled outer surfaces of the plates, a mother liquid is formed from the liquid feed mixture, which has a lower concentration of the substance to be separated and purified than the liquid feed mixture. The crystallization is conducted as long as necessary to separate the desired amount of substance to be separated and purified from the mother liquid. After completion of the crystallization, the mother liquid is completely removed from the crystallization vessel, the cooling of the plates is terminated and optionally the plates are heated so that the crystal layers formed on the outer surfaces of the plates melt, before the melt is removed from the crystallization vessel in order to obtain the separated and purified substance. Also in this case, in order to increase the purity of the target product the crystal layers may be sweated by gently heating them to a temperature close to the melting temperature of the purified substance in order to partially melt the crystals, before melting them. Moreover, the obtained substance may be further purified by another crystallization process or by a different process, such as distillation, if necessary.

However, known crystallization processes are still unsatisfying in particular in the case of the separation and purification of a substance from a liquid feed mixture including the substance to be separated and purified or target substance, respectively, in a comparable low concentration. An example thereof is the separation and purification of para-xylene from a raw hydrocarbon mixture, such as a refinery feedstock of aromatic $C_8$-mixtures including among others para-xylene, meta-xylene, ortho-xylene, ethylbenzene and the like and having a content of para-xylene of not more than about 20% by weight. Para-xylene is of significant industrial importance, because it is used as starting material for the manufacture of terephthalic acid, which again is the major constituent of polyethylene terephthalate (PET). However, known crystallization processes have an unsatisfyingly low crystallization efficiency in particular in the case of the separation and purification of a substance from a liquid feed mixture including the substance to be separated and purified in a comparable low amount of less than 70% by weight, of at most 50% by weight or even of at most 20% by weight. More specifically, the existing methods are expensive, require large plants and have a high energy demand when used for the separation and purification of a substance from a liquid feed mixture including the substance to be separated and purified in a low amount.

Taking this into account, the object underlying the present invention is to provide a process for the separation of a substance from a liquid feed mixture and for the purification of the substance by fractional layer crystallization, wherein the liquid feed mixture comprises the substance to be separated and purified in a concentration of less than 50% by weight, which has an improved crystallization efficiency and thus leads to a high yield of the target substance, which is cost efficient, which requires comparable small plants and which is energy efficient.

In accordance with the present invention this object is satisfied by a process for the separation of a substance from a liquid feed mixture and for the purification of the substance by fractional layer crystallization, wherein the liquid feed mixture comprises the substance to be separated and purified in a concentration of less than 50% by weight, comprising the steps of:

(a) feeding the liquid feed mixture into a crystallization zone, in which at least one surface is provided, so that at least a part of the surface contacts the liquid feed mixture,
(b) cooling the at least one surface of the crystallization zone to a temperature below the equilibrium freezing temperature of the liquid feed mixture so that a crystal layer enriched in the substance to be separated and purified is deposited on the at least one cooled surface, whereby a mother liquid having a lower concentration of the substance to be separated and purified than the liquid feed mixture is formed from the liquid feed mixture,
(c) removing at least a portion of the mother liquid from the crystallization zone,
(g) melting the crystal layer to obtain the separated and purified substance, wherein after step (c) and before step (g) the following steps are carried out:
(d) adding a further portion of liquid feed mixture into the crystallization zone,
(e) allowing further deposition of a crystal layer enriched in the substance to be separated and purified to take place on the at least one cooled surface and
(f) optionally carrying out a sweating stage and removing a sweating residue.

This invention bases on the surprising finding that by removing at least a part of the mother liquid, which is depleted in the substance to be separated and purified relative to the liquid feed mixture, from the crystallization zone after a certain time after starting the crystallization, that by adding afterwards a further portion of liquid feed mixture into the crystallization zone, which at least partially compensates the removed portion of mother liquid, and that by allowing further deposition of a crystal layer enriched in the substance to be separated and purified to take place on the at least one cooled surface after addition of the further portion of liquid feed mixture into the crystallization zone, the crystallization efficiency of the fractional layer crystallization process is significantly improved. Particularly, the crystallization process in accordance with the present invention leads to a notably high yield of the target substance and to a notably high crystal density. While with conventional suspension crystallization only up to 35% by volume of crystals can be obtained, the crystallization process in accordance with the present invention leads to a crystal density of up to 80% by volume of crystals. In addition, the crystallization process in accordance with the present invention is—in comparison to the known crystallization processes, when used for separating substances from mixtures containing the target substance in a low amount—more cost efficient, more energy efficient and requires smaller plants. The aforementioned effects and advantages are achieved in particular in the case that a liquid feed mixture is applied, which contains a comparable low amount of the substance to be separated and purified of less than 70% by weight based on 100% by weight of the initial liquid feed mixture added in step (a). Particularly good results are obtained even with liquid feed mixtures having an initial concentration of the substance to be separated and purified of at most 50% by weight or even of at most 20% by weight. Conventional fractional layer crystallization methods have—due to their limitations—not been successfully used for the purification of liquid mixture with such low amounts of the target substance. Without wishing to be bound to any theory or mechanism, it is assumed that the aforementioned advantages and effects are due to the following reasons.

Firstly, the mother liquid successively gets depleted in the substance to be separated and purified during conventional batch crystallization methods, which are described above. On account of this reason, in particular at the end of the operation of the conventional crystallization methods only a small amount of target material is included in the mother liquid so that only a very limited amount of the target material is available in the mother liquid for crystallization. Moreover, the successive depletion of the target substance in the mother liquid leads to a decrement of the concentration gradient between the crystallization surface, onto which already crystals enriched in the substance to be separated and purified are deposited, and the mother liquid, which further contributes to a reduction of the crystallization efficiency in conventional crystallization methods over the crystallization time. In contrast to this, liquid feed mixture having a higher concentration of the target substance than the mother liquid formed during the crystallization is preferably repeatedly introduced during the crystallization in the process in accordance with the present invention so that the depletion of the target substance in the mother liquid is at least partially and preferably completely compensated and thus the concentration of the target substance in the mother liquid is maintained substantially constant over the crystallization time. Due to this, more target material is present in the mother liquid over the crystallization time and the concentration gradient between the crystallization surface of the crystallizer, onto which already crystals enriched in the target substance are deposited, and the mother liquid is minimized as much as possible. This leads to an improved mass transfer and thus to an improved crystallization efficiency, even and particularly in the case that the target substance is contained in the liquid feed mixture in only small amounts.

Secondly, the partial removal of mother liquid from the crystallization zone in step (c) and the compensation of the removed liquid by the addition of liquid feed mixture into the crystallization zone in step (d) of the process in accordance with the present invention leads—in difference to the static crystallization methods known in the prior art, in which only mass transfer via diffusion takes place—to a convection of the mother liquid, which results in a forced movement or flow rate of the mother liquid and thus in a homogenization of the mother liquid. This leads in a static crystallizer to an improved mass transfer and thus to an improved crystallization efficiency, even and particularly in the case that the target substance is contained in the liquid feed mixture in only small amounts.

Due to the removal of a portion of the mother liquid from the crystallization zone in step (c) and the subsequent addition of a portion of liquid feed mixture into the crystallization zone in step (d), the method in accordance with the present invention allows a fractional layer crystallization method, which is conventionally performed as batch process, to be performed in a semi-continuous or even continuous manner.

In accordance with the present invention, the concentration of the substance to be separated and purified in the mother liquid may be measured by conventional methods, such as spectroscopic or chromatographic methods, preferably by gas chromatography-mass spectrometry. Moreover, the freezing temperature of the substance may be measured by conventional methods, such as differential scanning calorimetry (DSC).

In accordance with a particularly preferred embodiment of the present invention, only a portion of the mother liquid is removed in step (c) from the crystallization zone. This has the advantage that the portion of liquid feed mixture added into the crystallization zone in step (d) is mixed with the rest of the mother liquid remaining in the crystallization zone so that the liquid feed mixture added in step (d) is diluted by the rest of the mother liquid. Thereby, the equilibrium freezing temperature of the mother liquid is only slightly changed by the addition of the liquid feed mixture in step (d). In contrast thereto, if all of the mother liquid present in the crystallization zone is removed in step (c), the addition of the liquid feed mixture in step (d) leads to a comparable drastic change of the equilibrium freezing temperature of the mixture in the crystallization zone, because the liquid feed mixture has a higher concentration of the target substance than the removed mother liquid, which is depleted of the target substance. The change of the equilibrium freezing temperature of the mixture in the crystallization zone is in particular drastic when a complete or a substantially complete removal of a portion of the mother liquid according to step (c) is performed relatively late during the crystallization. Such a drastic change of the equilibrium freezing temperature of the mixture in the crystallization zone is—if the mixture is not appropriately pre-cooled—connected with the risk that crystals already deposited on the cooled surfaces melt and so target substance, i.e. substance to be separated from the liquid feed mixture and to be purified, is conveyed back from the crystal film into the mother liquid.

Good results are in particular obtained in the aforementioned embodiment when in step (c) 1 to 20% by volume and preferably 3 to 15% by volume, such as about 10% by volume, of the mother liquid is removed from the crystallization zone.

As set out above, one of the advantageous effects of the present invention in particular in a static fractional layer crystallization method is that the removal of a portion of the mother liquid from the crystallization zone in step (c) and the subsequent addition of a portion of liquid feed mixture into the crystallization zone in step (d) lead to a forced movement of the liquid in the crystallization zone and due to this to an improved mass transfer. As set out above, however, if too much of the mother liquid is removed in step (c) from the crystallization zone and subsequently compensated by the addition of respectively high amounts of liquid feed mixture in step (d), the equilibrium freezing temperature of the mixture in the crystallization zone may be changed too much so that crystals already deposited on the cooled surfaces may melt and target substance is conveyed back into the mother liquid. This is due to the fact that the freezing temperature of the mother liquid successively decreases over the crystallization time due to the decrement of the target substance having a higher freezing temperature than other components of the mother liquid. Accordingly, it is proposed in a further development of the idea of the present invention to recirculate a part, preferably 1 to 99% by volume, more preferably 20 to 80% by volume and most preferably 30 to 70% by volume of the portion of the mother liquid removed in step (c) into the crystallization zone, wherein preferably in step (d) a volume of liquid feed mixture is added into the crystallization zone which corresponds to the volume of the portion of the mother liquid removed in step (c), which is not recirculated into the crystallization zone. Thereby, the sum of the recirculated mother liquid and of the liquid feed added in step (d) determines the degree of forced movement in the mixture included in the crystallization zone, wherein only the amount of liquid feed added in step (d) contributes to a change of the equilibrium freezing temperature of the mixture in the crystallization zone. Thus, the combined addition of liquid feed in step (d) and of recirculated part of the mother liquid removed in step (c) allows a larger degree of forced movement in the mixture included in the crystallization zone than just the addition of liquid feed mixture in step (d). In this embodiment, preferably 10 to 50% by volume and more preferably 20 to 40% by volume of the mother liquid is removed from the crystallization zone in step (c) and 50 to 80% and preferably 60 to 70% of the removed mother liquid is recirculated to the crystallization zone. The remaining part of the removed mother liquid may be discarded, purified by any other or additional separation process or conveyed back into the production process.

In accordance with a further preferred embodiment of the present invention it is proposed to distribute the liquid feed mixture added in step (d) and thus also from the optionally recirculated portion of the mother liquid removed in step (c) at least substantially homogeneously over the horizontal cross-section of the crystallization zone, so that the concentration change of the mother liquid resulting from the addition of the portion of liquid feed mixture in step (d) is minimized in all parts of the mother liquid as much as possible. This assures that only the minimal change of the freezing temperature of the mother liquid possible results. In contrast thereto, if the portion of liquid feed mixture added in step (d) would be introduced at a specific point of the mother liquid present in the crystallization zone only, the concentration change of the mother liquid with regard to the target substance at this location would be drastic so that the freezing point of the mixture at this location of the crystallization zone would change drastically and thus crystals already deposited on the cooled surfaces near this location would melt.

In order to avoid an impairment of the crystals deposited on the cooled surface of the crystallization zone, it is further suggested to distribute the mother liquid and the liquid feed in the aforementioned embodiment so that only laminar flow occurs in the liquid contained in the crystallization zone, i.e. so that a turbulent flow of liquid is avoided in the crystallization zone. This is in particular preferred if the crystallization is carried out in a static crystallizer. Laminar flow means in accordance with the present invention a liquid flow, which does not cause that the crystals break off the crystal layer.

As set out above, after removal of a portion of the mother liquid in step (c) a further portion of liquid feed mixture is added into the crystallization zone in step (d), in order to increase the concentration of the target substance in the mixture present in the crystallization zone and in order to effect a forced movement of the mixture present in the crystallization zone so as to increase the crystallization efficiency of the process. Preferably, in step (d) the volume loss due to the removal of mother liquid in step (c) is compensated by the addition of (fresh) liquid feed mixture, i.e. so much liquid feed mixture is added in step (d) into the crystallization zone that the liquid level in the crystallization zone is the same as before the removal of mother liquid in step (c). Thus, if in step (c) a portion of the mother liquid is removed and completely discarded, the volume of added liquid feed mixture in step (d) is preferably identical or at least substantially identical to the volume of mother liquid removed in step (c). However, if a part of the mother liquid removed in step (c) is recirculated into the crystallization zone, the volume of added liquid feed mixture in step (d) is preferably the difference between the volume of the mother liquid removed in step (c) and the volume of the removed mother liquid recirculated into the crystallization zone.

As for the recirculation, it is preferred that the portion of liquid feed mixture is added in step (d) so that only laminar flow occurs in the mixture contained in the crystallization zone, in order to avoid an impairment of the crystals deposited on the cooled surface of the crystallization zone. This is in particular preferred if the crystallization is carried out in a static crystallizer.

In accordance with a further preferred embodiment of the present invention, the portion of the liquid feed mixture added in step (d) into the crystallization zone has the same temperature or at least substantially the same temperature as the liquid present in the crystallization zone before the addition of the portion of the liquid feed added in step (d).

The allowance of further deposition of a crystal layer enriched in the substance to be separated and purified to take place on the at least one cooled surface in accordance with step (e) is effected by maintaining the mother liquid in the crystallization zone for a time and under conditions so that crystal growth takes place. Thus, it is particularly preferred to keep the convection in the mother liquid so low that the crystal growth is not impaired and so low that crystals already deposited on the cooled surface are not detached from the cooled surface e.g. by turbulent flow. As a matter of course, step (e) is preferably performed after step (d).

In order to further increase the efficiency of the process, it is suggested in a further development of the idea of the present invention to repeat steps (c) to (e) for one or more times. The more often steps (c), (d) and (e) are repeated and the shorter the time periods between the repetitions of these steps, the more continuous the process in accordance with the present invention gets. However, since any removal of mother liquid according to step (c) and any addition of liquid feed mixture according to step (d) is energy intensive and consumes costly starting material, it is preferred to select the number of repetitions of steps (c) and (d) and to adjust the time span of step (e) so that a desired high crystallization efficiency is obtained with a minimum number of repetitions of steps (c) and (d) at a minimum operation time. For example, good results are obtained, when the crystallization step is finalized, when more than 70%, preferably more than 80% and most preferably more than 90% of the available crystal volume are used or occupied. Thus, the process according to the present invention is in fact a semi-continuous fractional layer crystallization process, even if it might be conducted theoretically even in a continuous manner or at least in a substantially continuous manner.

Preferably, the steps (c) to (e) are conducted so that the crystal density after the last step (e) is at least 20% by volume, more preferably at least 35% by volume, even more preferably at least 60% by volume and most preferably at least 75% by volume. The crystal density is defined in the present invention as the volume of the crystals based on the volume of liquid feed mixture initially added in step (a). For example, the crystal density may be determined by a turbidity measurement.

In order to increase the purity of the target product, it is preferable to perform at least one sweating step (f). Sweating means that the crystal layer(s) deposited on the cooled surface(s) are gently heated to a temperature close to the melting temperature of the purified substance in order to partially melt the crystals. Trapped and adherent melt, which contains the impurities, drains off during the partial melting of the crystals and is then removed from the crystallization zone. In order to conduct such a sweating, the surface, on which the crystals are deposited, is heated with a heat transfer medium to the desired temperature. Therefore, it is necessary to completely remove the mother liquid or at least substantially all of the mother liquid before starting step (f). On account of this reason, it is preferred that the optional step (f) is conducted after the last performance of step (e).

In accordance with a further preferred embodiment of the present invention, the crystallization is carried out in a falling film crystallizer. Such a dynamic crystallization process is advantageously fast and has a high capacity. In addition, falling film crystallization is characterized by an easy operation because there is no crystal slurry handling and no filtration, by a high reliability and by lower operation costs.

In accordance with an even more preferred embodiment of the present invention, the crystallization is carried out in a static crystallizer. This embodiment of the present patent application is particularly preferred, because the process in accordance with the present invention carried out in a static crystallizer allows—in comparison to the static crystallization processes known in the prior art, in which only mass transfer via diffusion take place—to significantly increase the degree of mass transfer from the mother liquid to the cooled surface(s), because the partial removal of mother liquid from the crystallization zone in step (c) and the compensation of the removed liquid by the addition of liquid feed mixture into the crystallization zone in step (d) leads to a convection of the mother liquid. This convection results in a forced movement of the mother liquid and thus in a homogenization of the mother liquid leading to an improved mass transfer and thus to an improved crystallization efficiency, even and particularly in the case that the target substance is contained in the liquid feed mixture in only small amounts. Thus, in contrast to conventional crystallization processes performed in static crystallizers, which are static, the crystallization process in accordance with the present invention is, if performed in a static crystallizer, semi-static. Moreover, in contrast to known static crystallization processes, which are batch processes, the process in accordance with this embodiment of the present invention is semi-continuously or even continuously or at least substantially continuously. Nevertheless, this embodiment of the present invention allows to additionally achieve the advantages of known static crystallization processes. More specifically, as conventional static crystallization processes the process in accordance with this embodiment of the present invention is well suited for crystallizing highly viscous liquids. Moreover, it has the advantage of high flexibility, of wide operation range, of easy operation since there is no crystal slurry handling and no filtration, of high reliability and of low operation costs due to the lack of moving parts.

It has been shown to be of further advantage, if the at least one cooled surface is arranged at least substantially vertical in the crystallization zone of the crystallizer used for carrying out the process in accordance with the present invention. This embodiment is in particular advantageous, if the process is performed in a static crystallizer. In accordance with the present invention, the term "substantially" means in connection with "vertical" or "horizontal" that the center line is within 5 degrees of the vertical or horizontal axis, respectively.

After the last performance of step (e), the mother liquid is completely removed from the crystallization zone, then the crystalline layer is melted in step (g) and finally the melted product is removed from the crystallization zone, in order to obtain the separated and purified substance. If the optional sweating according to step (f) is performed, step (g) is performed after step (f).

Optionally, the separated and purified substance obtained in step (g) may be further purified in a subsequent separation process. The subsequent separation process may be a crystallization process, such as a melt crystallization process, and in particular the repetition of the process in accordance with the present invention described above. In the last mentioned case, the obtained product is used as liquid feed mixture in step (a) and steps (b) to (f) are repeated.

Alternatively, the subsequent separation process may be a mechanical or a different thermal separation process, such as a distillation process. However, it is preferred particularly for heat-sensitive substances that the optional subsequent separation process is a crystallization process and more preferably a melt crystallization process, because this is mild compared to other thermal separation processes, such as distillation.

It is also possible to combine both aforementioned embodiments, for example by firstly further purifying the product obtained in step (e) by a subsequent crystallization and then by a subsequent distillation or other thermal or mechanical separation process.

As set out above, the process in accordance with the present invention is particularly suitable for the purification of liquid mixtures having low to very low concentrations of the target substance. On account of this it is preferred to use in the process and in particular in steps (a) and (d) a liquid feed mixture having an initial concentration of the substance to be separated and purified of less than 50% by weight. More preferably a liquid feed mixture is used, which has an initial concentration of the substance to be separated and purified of less than or equal to 30% by weight, even more preferably of less than or equal to 25% by weigh and most preferably of less than or equal to 20% by weight. Conventional fractional layer crystallization processes with liquid feed mixture having such low concentrations of the target substance would suffer the disadvantage of unutilized cooled surface area, which is energetically inefficient. Moreover, in traditional processes a larger number of crystallizers would be needed to purify such low concentrated liquid feed mixtures.

In principle, the method in accordance with the present invention is not limited concerning the composition of the liquid feed mixture. Good results are in particular achieved with a liquid feed mixture, which is derived from a biomass process and preferably from a biomass process comprising a fermentation step. Streams from biomass and fermentation processes are quite favorable for use in the process in accordance with the present invention, because they are quite diluted due to the high concentration of water or other solvent or other impurities. A biomass process is in accordance with the present invention a process to obtain compounds or substances from plant or animal source materials.

For example, the substance to be separated and purified from the liquid feed mixture may be selected from the group consisting of xylene, durene, caprolactam, lactic acid, sorbitol, sorbitan, isosorbide, phytosterol, fatty acids, fatty acid esters, paraffins, bisphenols and any arbitrary combination of two or more of the aforementioned substances. Many of these compounds may be produced by a fermentation process or in a commercial manufacturing process that result in relatively low concentrations or in dilute streams, such as waste streams, from isomerization processes and the like. The process in accordance with the present invention allows to separate the target substance in a high yield from such a liquid feed mixture.

The process in accordance with the present invention is in particular suitable for separating and purifying para-xylene from a liquid feed mixture comprising para-xylene in comparable low amounts, such as from a refinery feedstock of aromatic $C_8$-mixtures including among others para-xylene, meta-xylene, ortho-xylene, ethyl benzene and the like and having a content of para-xylene of at most 50% by weight, preferably of at most 30% by weight, more preferably of at most 25% by weight and most preferably of at most 20% by weight, or such as from a liquid feed mixture obtained by a biomass process comprising one or more fermentation steps and having a content of para-xylene of at most 30% by weight, preferably of at most 25% by weight and more preferably of at most 20% by weight.

According to a further aspect the present invention relates to a plant for the separation and purification of a substance in a concentration of less than 50% by weight, which is embodied to carry out the process as described above and which comprises:

(a) a source of the liquid feed mixture comprising the substance to be separated and purified in a concentration of less than 50% by weight, (b) a static crystallization apparatus, wherein the static crystallization apparatus comprises:
(c) a vessel,
(d) a substantially vertically-disposed cooled surface,
(e) optionally a crystal-retention system for retaining crystals within the vessel,
(f) a liquid inlet distribution system embodied so as to distribute a liquid substantially homogeneously over a horizontal cross-section of the vessel and
(g) a liquid outlet collection system embodied so as to collect liquid homogeneously along an edge between a substantially vertical wall and a bottom of the vessel, wherein the static crystallization apparatus additionally comprises a circulation loop, wherein the circulation loop is embodied to provide at least a partial recirculation between the liquid outlet collection system and the liquid inlet distribution system.

Due to the configuration of the liquid inlet distribution system according to feature (f), the static crystallization apparatus allows to at least substantially homogeneously distribute the liquid feed added in step (d) of the crystallization process described above and thus also from the optionally recirculated portion of the mother liquid removed in step (c) over the horizontal cross-section of the crystallization zone from above, so that the concentration change of the mother liquid resulting from the addition of the portion of liquid feed mixture in step (d) is minimized in all parts of the mother liquid as much as possible. This assures that only the minimal change possible of the freezing temperature of the mother liquid results. In contrast thereto, if the portion of liquid feed added in step (d) would be introduced at a specific point of the mother liquid present in the crystallization zone only, the concentration change of the mother liquid at this location would be drastic so that the freezing point of the mixture at this location of the crystallization zone would change drastically and thus crystals already deposited on the cooled surfaces near this location would melt. The liquid inlet distribution system preferably comprises a liquid distributor, which may comprise pipes or channels connected to a set of liquid outlets, such as nozzles, jets, valves or channels distributed over the horizontal cross section of the crystallization zone. In particular, respective liquid inlet distribution systems used in distillation columns may be used, such as for example those as disclosed in "Internals for packed columns" from Sulzer Chemtech (brochure 22.51.06.40-V.13-20).

The circulation loop may comprise a pump and pipes or other liquid distribution channels in fluid communication with each other as well as with the liquid inlet distribution system (f) and with the liquid outlet collection system (g). As described above for the crystallization method, this allows to increase the forced movement of the liquid in the crystallization zone and due to this to improve the mass transfer, without unnecessary increase of the freezing temperature after addition of the portion of liquid feed mixture in step (d). This is due to the fact that in this embodiment the sum of the mother liquid recirculated via the circulation loop and of the liquid feed mixture added in step (d) determines the degree of forced movement in the mixture included in the crystallization zone, wherein only the amount of liquid feed mixture added in step (d) contributes to a change of the equilibrium freezing temperature of the mixture in the crystallization zone.

Due to the configuration of the liquid outlet collection system according to feature (g), the static crystallization apparatus allows to collect liquid homogeneously along an edge between a substantially vertical wall and a bottom of the vessel. The collected liquid is a substantially crystal-free liquid obtained after the crystallization process described above. The crystals formed in this crystallization process will generally be retained on the substantially vertically-disposed cooled surfaces (d) within the crystallization zone (attached crystals), optionally any detached crystals will be retained by the crystal-retention system (e), which may be a sieve, strainer, sifter, colander or screen. In some embodiments, it is preferred that the liquid outlet collection system (g) collects liquid homogeneously along one or two pairs of two preferably oppositely-arranged edges, each between a substantially vertical wall and a bottom of the vessel. This assures that there are no dead zones in the liquid flow field within the crystallization zone. The liquid outlet collection system (g) preferably comprises a series of nozzles, holes or other openings along the edge(s) between the substantially vertical wall(s) and the bottom of the vessel. This series of nozzles, holes or other openings is in fluid communication with the circulation loop.

Moreover, it is proposed in a further preferred embodiment of the present invention that the static crystallization apparatus additionally comprises an overflow prevention system embodied so as to maintain a desired liquid level in the vessel. For example, as liquid overflow prevention system U-tube siphons or the like may be used. This embodiment is particularly preferred, if a static crystallizer is used.

Particularly in the case that a falling film crystallizer is used, the crystallization apparatus preferably comprises an external tank or buffer vessel equipped with a liquid level sensor, in order to control that during the method the volume of liquid withdrawn from the crystallizer is equal to the volume of liquid, which is fed into the crystallizer.

Figure 2:
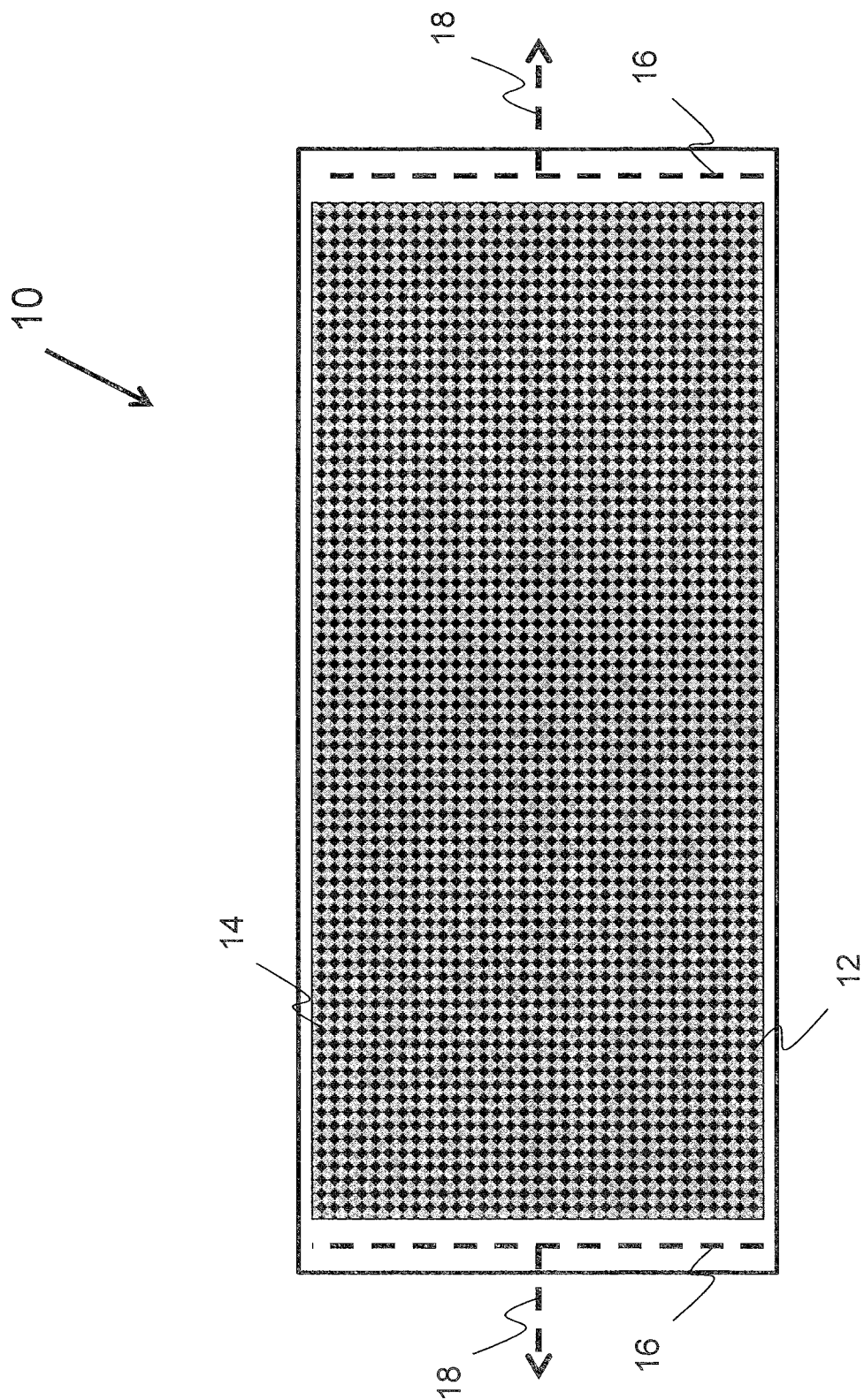
Figure 3:
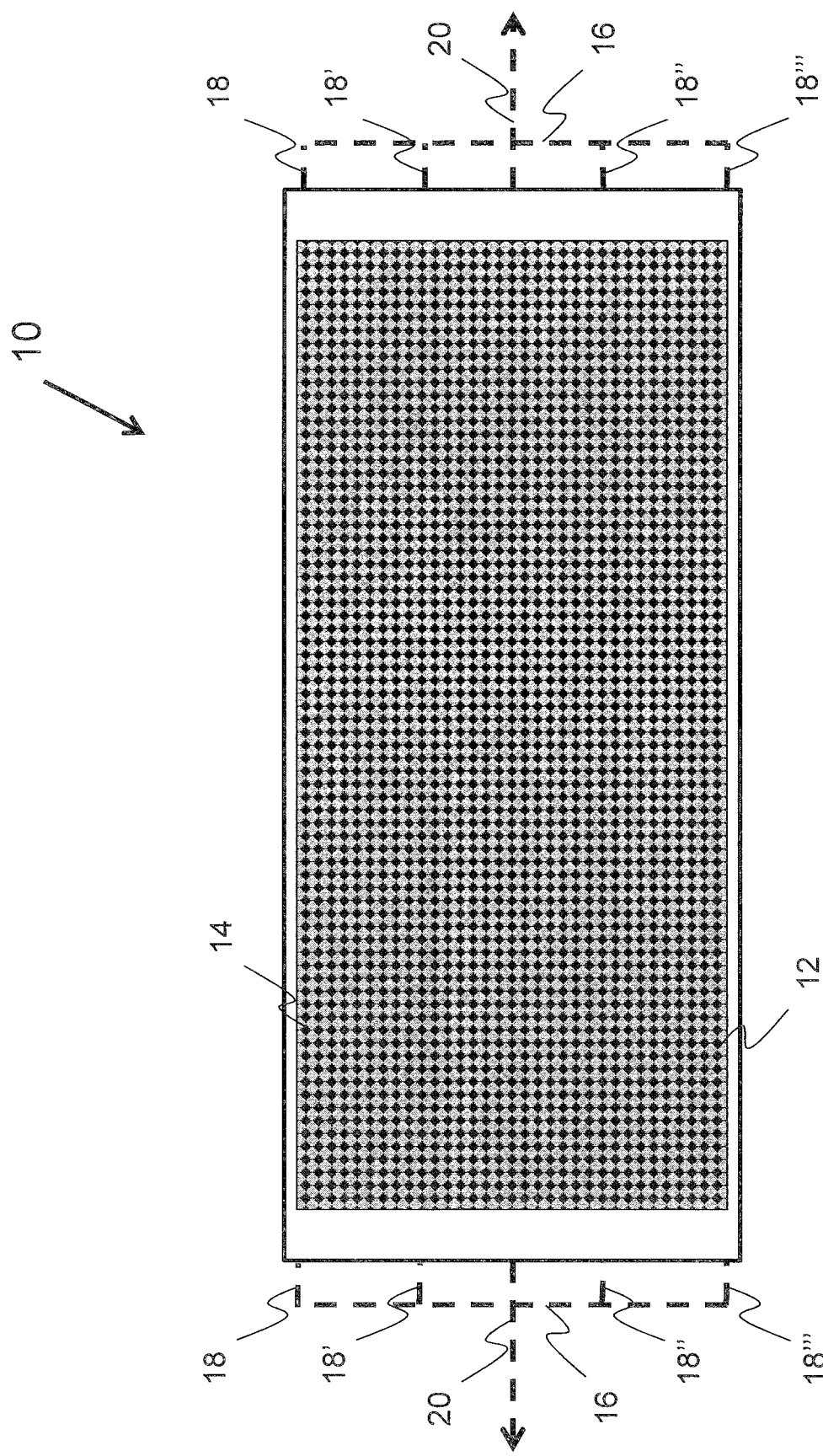

The invention will be explained in more detail hereinafter with reference to the drawings, in which:

FIG. 1 schematically shows a crystallization apparatus according to a first embodiment, which is embodied to be suitable for the process in accordance with the present invention, in vertical cross-section, FIG. 2 schematically shows the crystallization apparatus of FIG. 1 in horizontal cross-section and FIG. 3 schematically shows a crystallization apparatus according to a second embodiment, which is embodied to be suitable for the process in accordance with the present invention, in horizontal cross-section.

FIGS. 1 and 2 schematically show a crystallization apparatus 10 according to one embodiment of the invention in vertical and horizontal cross-section. The crystallization apparatus 10 comprises a plurality of vertically arranged cooled plates 12, onto which the substance to be separated and purified deposit during the operation of the crystallization apparatus 10. A liquid inlet distribution system 14 is arranged at the upper part of the crystallization apparatus 10 above the cooled plates 12 and embodied so as to distribute the mother liquid substantially homogeneously over the horizontal cross-section of the crystallization apparatus 10. Moreover, the crystallization apparatus 10 comprises on both sides in the bottom part each a liquid outlet collection system 16 embodied so as to collect liquid homogeneously along both sides, which is then withdrawn from the crystallization apparatus 10 via the outlet line 18 or alternatively recirculated via circulation loop 22 by means of pump 24.

The crystallization apparatus 10 of FIG. 3 is similar to that shown in FIGS. 1 and 2, but comprises on both sides each four outlet lines 18, 18', 18", 18''', which merge into one central outlet line 20. This effects an even more homogenous flow field than that obtained with the crystallization apparatus 10 shown in FIGS. 1 and 2.

REFERENCE NUMERALS

10 Crystallization apparatus
12 Cooled plates
14 Liquid inlet distribution system
16 Liquid outlet collection system
18, 18', 18", 18'" Outlet line
20 Central outlet line
22 Circulation loop
24 Pump

The invention claimed is:

1. A plant for the separation and purification of a substance in a concentration of less than 50% by weight, the plant comprising:
   (a) a source of the liquid feed mixture comprising the substance to be separated and purified in a concentration of less than 50% by weight,
   (b) a static crystallization apparatus,
   wherein the static crystallization apparatus comprises:
   (c) a vessel,
   (d) a substantially vertically-disposed cooled surface,
   (e) optionally a crystal-retention system for retaining crystals within the vessel,
   (f) a liquid inlet distribution system embodied so as to distribute a liquid substantially homogeneously over a horizontal cross-section of the vessel and
   (g) a liquid outlet collection system embodied so as to collect liquid homogeneously along an edge between a substantially vertical wall and a bottom of the vessel,
   wherein the static crystallization apparatus additionally comprises a circulation loop connected directly between the liquid outlet collection system and the liquid inlet distribution system, wherein the circulation loop is embodied to provide at least a partial recirculation directly between the liquid outlet collection system and the liquid inlet distribution system.

2. The plant of claim 1, wherein the static crystallization apparatus additionally comprises an overflow prevention system embodied so as to maintain a desired liquid level in the vessel.

* * * * *